United States Patent [19]

Fry

[11] Patent Number: 4,582,061
[45] Date of Patent: Apr. 15, 1986

[54] NEEDLE WITH ULTRASONICALLY REFLECTIVE DISPLACEMENT SCALE

[75] Inventor: Francis J. Fry, Indianapolis, Ind.

[73] Assignee: Indianapolis Center for Advanced Research, Inc., Indianapolis, Ind.

[21] Appl. No.: 322,538

[22] Filed: Nov. 18, 1981

[51] Int. Cl.⁴ ............................................. A61B 17/34
[52] U.S. Cl. .................................. 128/329 R; 128/654; 128/660
[58] Field of Search .................... 128/329 R, 660–661, 128/2, 754, 653–654, 751, 754, 24 A; 604/158

[56] References Cited

U.S. PATENT DOCUMENTS

| | | | |
|---|---|---|---|
| 3,556,079 | 1/1971 | Omizo | 128/661 |
| 3,687,142 | 8/1972 | Leibinzohn | 128/658 |
| 3,792,703 | 2/1974 | Moorehead | 604/158 |
| 4,029,084 | 6/1977 | Soldner | 128/660 |
| 4,058,114 | 11/1977 | Soldner | 128/660 |
| 4,096,862 | 6/1978 | DeLuca | 128/656 |
| 4,249,539 | 2/1981 | Vilkomerson et al. | 128/754 X |
| 4,279,252 | 7/1981 | Martin | 128/658 X |
| 4,346,717 | 8/1982 | Haerten | 128/660 |
| 4,373,532 | 2/1983 | Hill et al. | 128/660 |

FOREIGN PATENT DOCUMENTS

| | | | |
|---|---|---|---|
| 2911354 | 2/1980 | Fed. Rep. of Germany | 128/660 |
| 2919024 | 7/1980 | Fed. Rep. of Germany | 128/660 |
| 2942405 | 4/1981 | Fed. Rep. of Germany | 128/660 |
| 2946662 | 5/1981 | Fed. Rep. of Germany | 128/662 |

*Primary Examiner*—Kyle L. Howell
*Assistant Examiner*—Angela D. Sykes
*Attorney, Agent, or Firm*—Woodard, Weikart, Emhardt & Naughton

[57] ABSTRACT

A puncturing device for insertion into the body, which has an ultrasonically coded displacement scale of gaseous inclusions regularly spaced along the length of the device. Owing to the acoustic reflectiveness of the gaseous inclusions, the precise location of the puncturing device can be directly and readily detected by an ultrasound visualization system. The acoustically reflective displacement scale enables the calibration of distances to be made directly from the ultrasound viewing screen. Located at the tip of the puncturing device is a gaseous inclusion which reveals the precise location of the tip of the device in the body.

12 Claims, 6 Drawing Figures

NEEDLE WITH ULTRASONICALLY REFLECTIVE DISPLACEMENT SCALE

BACKGROUND OF THE INVENTION

1. Field of the Invention.

The field of the invention is puncturing devices for insertion into the body. More particularly, the field of the invention is such devices which are inserted into the body under the guidance of an ultrasound visualization system.

2. Brief Description of the Prior Art.

It is known in the prior art to insert a puncturing cannula into the body under the guidance of an ultrasound visualization system aimed at the area of puncture. U.S. Pat. No. 3,556,079 to Omizo and U.S. Pat. No. 4,029,084 to Soldner are two patents relating to ultrasonically guided puncturing cannula apparatus.

Under certain circumstances however, the needle can not be directly viewed by the ultrasound visualization system. For instance, at the point of entry into the body the puncturing cannula is typically not within the scanning region of the ultrasound system. U.S. Pat. No. 4,058,114 to Soldner discloses an ultrasound puncturing guidance system which utilizes an aiming pin, superimposed over the viewing screen, to aid in the aiming and locating of the puncturing needle. U.S. Pat. No. 4,058,114 also discloses the use of a displacement scale system in which the needle position and distance calibration are indirectly determined by referring to displacement markings on the aiming pin.

The needle is sometimes not visible on the viewing screen even when it is within the scanning region. This is because the difference in the reflective properties of the needle and the surrounding tissue is sometimes not sufficient enough to make the needle distinguishable. The tendency of the needle to disappear on the viewing screen is accentuated at sharper angles of insertion into the body (approaching 90° with respect to the body surface—depending on the area being probed, the needle may become difficult to detect at an angle of incidence of as little as 45° or less). The needle may also disappear from the viewing screen if it bends slightly away from the scanning plane during the insertion process.

SUMMARY OF THE INVENTION

The present invention relates to the enhancement of the viewability of puncturing devices within the body by ultrasound visualization systems, and to distance calibration during ultrasound scanning procedures. In certain embodiments, a puncturing device for insertion into the body is ultrasonically coded by gaseous inclusions that are regularly spaced along the length of the device. The acoustical reflectiveness of the gaseous inclusions enhances the direct detection of the puncturing device within the body by an ultrasound visualization system. Collectively, the inclusions constitute an acoustically reflective displacement scale that enables the calibration of distances to be made directly from the ultrasound viewing screen. A gaseous inclusion at the tip of the puncturing device reveals the precise location of the tip of the body. Further objects and advantages will become apparent from a reading of the following disclosure.

DESCRIPTION OF THE PREFERRED EMBODIMENTS

Figure 1:
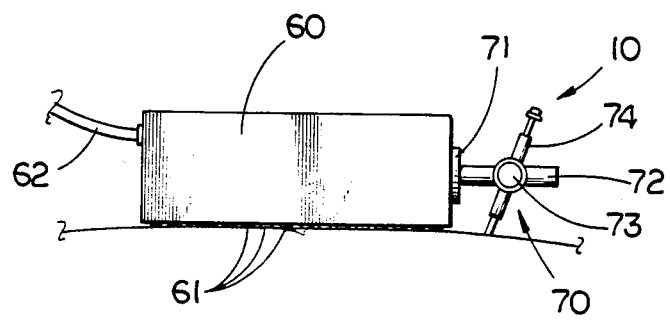
FIG. 1 is a side view of an ultrasound transducer apparatus in position for viewing the internal structure of a portion of the body. Mounted to the transducer apparatus is an adjustable cannula guide which is slidably receiving a puncturing device of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, in FIG. 1 an ultrasound transducer apparatus 60 is being applied to the body of a patient. A linear phased array of transducers 61 sequentially transmit ultrasound pulses into the body and receive echos therefrom. The sequential excitation of the transducers is controlled by, and the resulting echoes are processed by, ultrasound visualization circuitry (not shown) through cable 62.

Mounted to transducer apparatus 60 is guide apparatus 70. Guide apparatus 70 includes rotatable mounting plate 71 which allows a rocking motion between guide 70 and transducer 60 (relative rotational motion about the longitudinal axis of bar 72). This rocking capability aids the technician in maintaining the inserted needle 10 along the scanning plane. Attached to bar 72 is knob 73. Knob 73 is slidable along bar 72 and can be tightened to any desired position along bar 72. When fixed in position, knob 73 also sets the approach angle of tube 74, whereby the angle of insertion of puncturing device 10 into the body can be selected. Puncturing device 10 is slidably received by guiding tube 74 and inserted into the body.

Figures 3, 4, 5, 6:
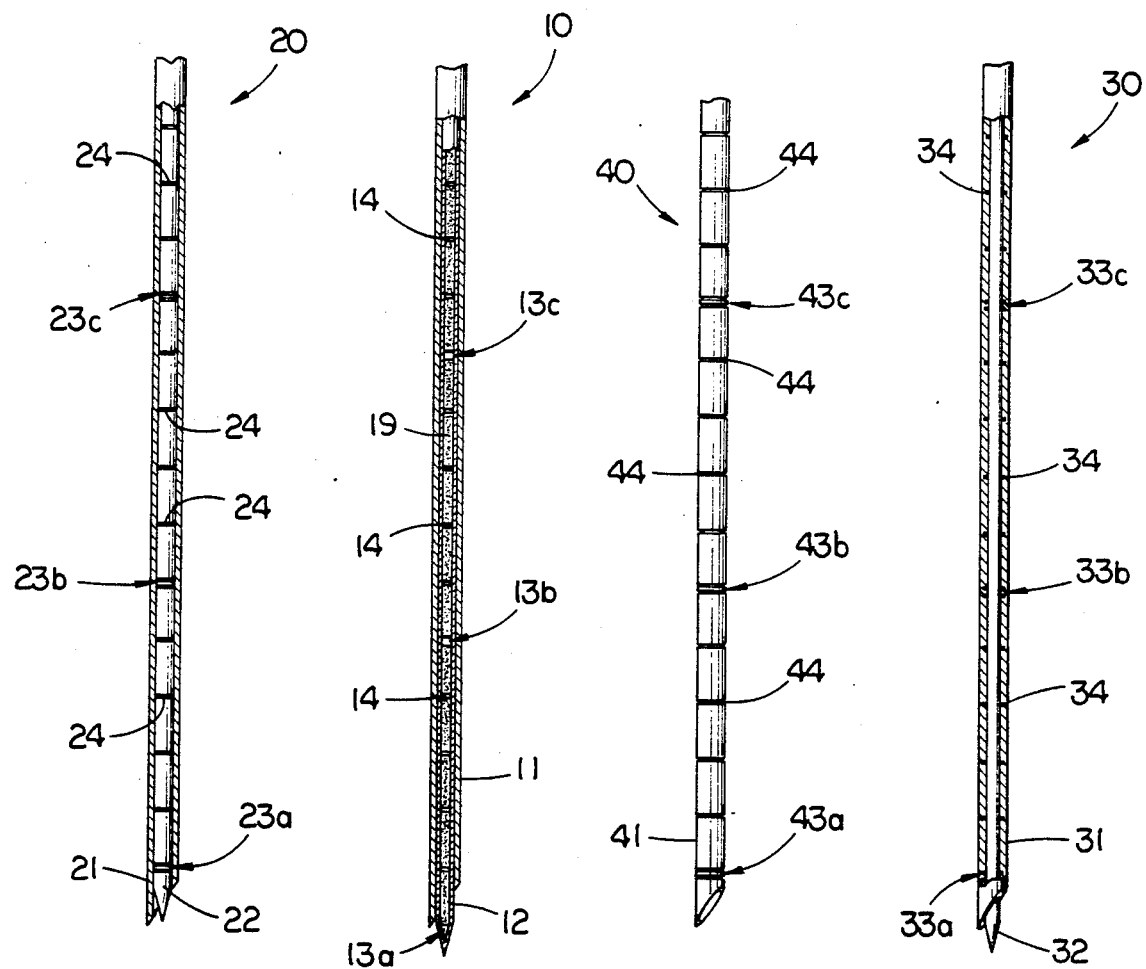
FIG. 3 is a fragmentary, partially sectioned view of the puncturing device of FIG. 1 having an acoustically reflective displacement scale which includes regularly spaced gaseous inclusions within its stylette.
FIG. 4 is a fragmentary, partially sectioned view of a second puncturing device having regularly spaced annular grooves on its stylette.
FIG. 5 is a fragmentary, partially sectioned view of a third puncturing device which includes regularly spaced annular grooves on the interior surface of the puncturing cannula.
FIG. 6 is a fragmentary, side view of a puncturing needle in which the acoustically reflective displacement scale includes annular grooves on the outside of the needle.

Puncturing device 10 incorporates an acoustically reflective displacement scale, thereby enhancing its detectability by ultrasound and providing direct distance calibration during scanning procedures. FIG. 3 illustrates the manner in which the acoustically reflective displacement scale is incorporated by puncturing device 10. Puncturing device 10 includes a hollow puncturing needle 11 and a stylette 12 which is slidably received by needle 11. Needle 11 and stylette 12 are inserted, in combination, into the body. Gaseous inclusions are regularly spaced within stylette 12 along its length.

The acoustic reflectiveness of the gaseous inclusions makes the precise location of device 10 within the body clearly detectable by an ultrasound visualization system. Gaseous inclusion 13a is positioned directly at the tip of stylette 12, thereby enhancing the visualization of the tip of the needle. Collectively, the gaseous inclusions form an acoustically reflective displacement scale, whereby the calibration of distances can be made directly on an ultrasound viewing screen. For instance, inclusion 13a and 13b are spaced apart 5 cm. Likewise, inclusion 13b and 13c are also spaced apart 5 cm. Minor gaseous inclusions 14 trap less gas, and therefore are not as reflective as, inclusions 13a, 13b, and 13c. Inclusions 14 are regularly spaced at intervals of 1 cm. between inclusions 13a and 13b, and between inclusions 13b and 13c, thereby completing the acoustically reflective displacement scale.

Figure 2:
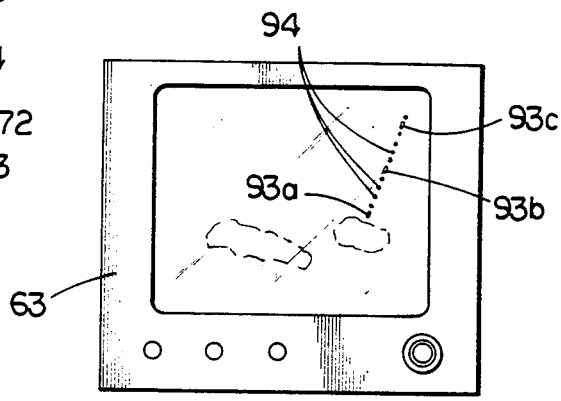
FIG. 2 shows a viewing screen which is displaying internal body structure by means of ultrasound visualizatin.

FIG. 2 represents the manner in which the displaying of puncturing device 10 on an ultrasound visualization screen 63 is enhanced by its acoustically reflective displacement scale. Regularly spaced illuminations 94, corresponding to inclusions 14, reveal the position of the puncturing device 10 within the body. Enlarged illumination 93a corresponds to inclusion 13a and indicates the position of the tip of stylette 12. Subsequent enlarged illuminations 93b and 93c correspond to inclusions 13b and 13c. Because the inclusions are regularly spaced within stylette along its length in the format of a displacement scale, distances can be readily ascertained directly from viewing screen by making reference to the iluminations on the screen.

FIG. 4 discloses a puncturing device 20 which includes a needle 21 and stylette 22 combination similar to device 10 in FIG. 3, however the acoustically reflective displacement scale is incorporated in device 20 by annular grooves on stylette 22 rather than by inclusions within the stylette. Grooves 24 are regularly spaced at 1 cm. intervals. 5 cm. spacing is denoted by grooves pairs 23a, 23b, and 23c.

FIG. 5 discloses a third type of puncturing device 30 incorporating an acoustically reflective displacement scale. In FIG. 5 annular grooves (including single grooves 34 spaced apart 1 cm. and groove pairs 33a, 33b, 33c with 5 cm. spacing) on the inside of hollow puncturing needle 31 formulate the displacement scale. Gas bubbles are trapped between stylette 32 and needle 31 in the grooves, thereby creating points of high acoustic reflectiveness which can be readily detected by an ultrasound visualization system and appear as illuminations on an ultrasound viewing screen, such as screen 63. Puncturing device 20 of FIG. 4 also creates points of high acoustic reflectiveness by trapping gas bubbles in grooves between the stylette (22) and the needle (21).

In FIG. 6, hollow puncturing needle 40 has annular grooves (i.e. groove pairs 43a, 43b, and 43c, and grooves 44) on its outside surface which are regularly spaced to form an acoustically reflective displacement scale. In this embodiment, gas bubbles are trapped in the grooves between needle 40 and the surrounding body tissue.

While there have been described above the principles of this invention in connection with specific apparatus and techniques, it is to be clearly understood that this description is made only by way of example and not as a limitation to the scope of the invention.

What is claimed is:

1. A probe for insertion into the body, said probe comprising: an elongated probe body, having a distal end and a proximal end penetrating means for penetrating said probe body into the body, said penetrating means including a penetrating tip located at the distal end of said probe body; and acoustic reflector means, located at the penetrating tip, for creating a spot of high acoustic reflectiveness at said penetrating tip, said acoustic reflector means including gaseous inclusion means for trapping a gas pocket within said probe, whereby the location of the tip of said probe body can be readily detected by an ultrasound visualization system.

2. A surgical puncturing device comprising:
   (a) a hollow puncturing cannula;
   (b) a stylette, slidably received by said puncturing cannula, said stylette being suitable for insertion into the body in combination with said puncturing cannula; and
   (c) ultrasonically reflective displacement scale means for incorporating in said puncturing device an ultrasonically reflective displacement scale that is detectible by an ultrasound visualization system, said means including a plurality of gas trapping means for trapping gas pockets within said puncturing device, said plurality of gas trapping means being regularly spaced along said puncturing cannula.

3. The surgical puncturing device of claim 2 in which said gas trapping means include a series of cavities within said stylette.

4. The surgical puncturing device of claim 2 in which said gas trapping means include a series of annular grooves in said stylette.

5. The surgical puncturing device of claim 2 in which said gas trapping means include a series of annular grooves on the interior of said hollow puncturing cannula.

6. The surgical puncturing device of claim 2 in which said gas trapping means include major gas trapping means and minor gas trapping means, said major gas trapping means including means for trapping more gas than is trapped by said minor gas trapping means, said major gas trapping means being spaced at regular intervals along said puncturing cannula, said minor gas trapping means being spaced apart at regular intervals between adjacent major gas trapping means.

7. The surgical puncturing device of claim 6 in which said major gas trapping means are spaced apart at intervals of about 5 cm. and said minor gas trapping means are spaced apart at intervals of about 1 cm.

8. The surgical puncturing device of claim 2 in which the spacing between adjacent gas trapping means is about one centimeter.

9. A probe for insertion into the body, said probe comprising: an elongated probe body, penetrating means for penetrating said probe body into the body; and ultrasonically reflective displacement scale means for incorporating in said probe an ultrasonically reflective displacement scale that is detectible by an ultrasound visualization system, said means including a plurality of gas trapping means for trapping gas pockets within said probe body, said plurality of adjacent gas trapping means being regularly spaced along said probe body.

10. The probe of claim 9 in which the spacing between adjacent gas trapping means is approximately one centimeter.

11. The probe of claim 9 in which said gas trapping means include major gas trapping means and minor gas trapping means, said major gas trapping means including means for trapping more gas than is trapped by said minor gas trapping means, said major gas trapping means being spaced at regular intervals along said probe body, said minor gas trapping means being spaced apart at regular intervals between adjacent major gas trapping means.

12. The probe of claim 9 in which said major gas trapping means are spaced apart at intervals of about 5 cm. and said minor gas trapping means are spaced at intervals of about 1 cm.

* * * * *